United States Patent [19]

Dodd

[11] 4,180,686

[45] Dec. 25, 1979

[54] OXIDATIVE COUPLING OF ALKYLPHENOLS

[75] Inventor: John R. Dodd, Ponca City, Okla.

[73] Assignee: Conoco, Inc., Ponca City, Okla.

[21] Appl. No.: 6,419

[22] Filed: Jan. 25, 1979

[51] Int. Cl.$^2$ ............................................. C07C 37/00
[52] U.S. Cl. ............................... 568/730; 260/396 N
[58] Field of Search ..................... 568/730; 260/396 N

[56] References Cited

U.S. PATENT DOCUMENTS

| | | | |
|---|---|---|---|
| 2,885,444 | 5/1959 | Fookes et al. | 568/730 |
| 3,153,098 | 10/1964 | Boag | 568/730 |
| 3,562,338 | 2/1971 | Zaweski | 568/730 |
| 3,631,208 | 12/1971 | Hay | 568/730 |
| 3,873,627 | 3/1975 | Lee et al. | 568/730 |
| 4,070,383 | 1/1978 | Rutledge | 568/730 |
| 4,085,124 | 4/1978 | Rutledge | 568/730 |
| 4,086,253 | 4/1978 | Hopper et al. | 260/396 N |
| 4,093,598 | 6/1978 | Banucci et al. | 260/47 ET |
| 4,096,190 | 6/1978 | Rutledge | 568/730 |
| 4,098,766 | 7/1978 | Rutledge | 568/730 |
| 4,098,830 | 7/1978 | Rutledge | 568/730 |
| 4,100,202 | 7/1978 | Rutledge | 568/730 |
| 4,100,203 | 7/1978 | Rutledge | 568/730 |
| 4,100,204 | 7/1978 | Rutledge | 568/730 |
| 4,100,205 | 7/1978 | Rutledge | 568/730 |
| 4,100,206 | 7/1978 | Rutledge | 568/730 |
| 4,101,561 | 7/1978 | Rutledge | 568/730 |
| 4,108,908 | 8/1978 | Rutledge | 568/730 |
| 4,132,722 | 1/1979 | Rutledge | 568/730 |
| 4,139,544 | 2/1979 | Rutledge | 568/730 |

FOREIGN PATENT DOCUMENTS 566274  5/1974  Switzerland ............................. 568/730

*Primary Examiner*—Norman Morgenstern
*Attorney, Agent, or Firm*—Bayless E. Rutherford, Jr.

[57] ABSTRACT

A method of preparing carbon-carbon coupled condensation products of alkylphenols is disclosed. Briefly, the method comprises oxidation of certain specific alkylphenols using palladium acetate as the catalyst in acetic acid or other suitable solvent.

12 Claims, No Drawings

OXIDATIVE COUPLING OF ALKYLPHENOLS

FIELD OF THE INVENTION

The invention is in the general field of preparing carbon-carbon coupled condensation products of alkylphenols.

GENERAL BACKGROUND

The preparation of carbon-carbon coupled condensation products of alkylphenols is well-known in the art. The preparation generally uses oxygen and a catalyst (e.g. ferric chloride).

The procedure can be illustrated as follows:

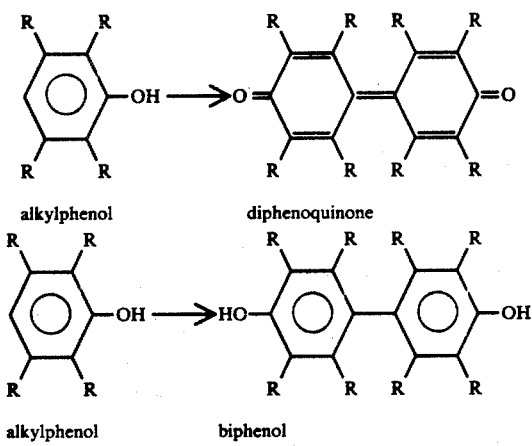

R is usually either hydrogen or an alkyl group in the above.

Biphenols are useful as antioxidants, stabilizers and as intermediates in the synthesis of various polymers, particularly polyesters. Diphenoquinones are useful as antioxidants.

I have discovered an improved method of preparing carbon-carbon coupled condensation products of certain alkylphenols which uses palladium acetate as the catalyst.

The process possesses several advantages. First, it produces the desired product in high selectivity. Second, greater ease in product isolation is possible since only a small (i.e. catalytic) amount of palladium acetate is required.

BRIEF SUMMARY OF THE INVENTION

Briefly stated, the present invention is directed to a method of preparing carbon-carbon coupled condensation products of an alkylphenol, wherein said method comprises contacting said alkylphenol with an effective amount of oxygen or an oxygen-containing gas under reaction-promoting conditions in the presence of an effective amount of palladium acetate catalyst in a polar solvent which solubilizes palladium acetate.

The alkylphenols used in the method are represented by the formula

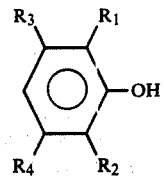

wherein $R_1$, $R_2$, $R_3$ are $R_4$ are hydrogen or a $C_1$ to $C_4$ alkyl. Of $R_1$, $R_2$, $R_3$ and $R_4$, at least two, preferably three, must contain alkyl groups. When only two alkyl groups are present one must be in a position meta to the hydroxyl group.

DETAILED DESCRIPTION

Alkylphenols which are used in my invention are represented by the formula

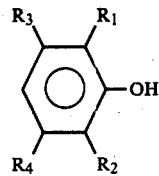

wherein $R_1$, $R_2$, $R_3$ and $R_4$ are hydrogen or a $C_1$ to $C_4$ alkyl. Of $R_1$, $R_2$, $R_3$ and $R_4$, at least two, preferably three, must contain alkyl groups. When only two alkyl groups are present one must be in a position meta to the hydroxyl group.

In order to prepare a product containing mainly biphenols at least three of the R groups must contain alkyl groups. Use of an alkylphenol with only two alkyl substituents results in a product containing a significant amount of diphenoquinone in addition to the biphenol.

Either oxygen or an oxygen-containing gas such as air can be used in my process. When using air larger quantities must be used in order to provide the required amount of oxygen.

Divalent palladium acetate (Pd(OAc)$_2$) is used in my invention.

Suitable solvents for my process are polar solvents which solubilize palladium acetate. Examples of suitable solvents include acetic acid, $C_1$–$C_3$ alkanols, acetonitrile and N,N-dimethylformamide. Acetic acid is the preferred solvent. While glacial acetic acid is preferred, the use of aqueous acetic acid containing as much as 20 weight percent water is also suitable.

The relative amounts of materials used in my process are shown in the following table.

|  | Suitable | Preferred |
|---|---|---|
|  | (moles) | |
| Phenol | 1.0 | 1.0 |
| Oxygen* | 2.5–100 | 10–50 |
| Solvent | 2–30 | 4.5–30 |
| Palladium acetate | 0.001–0.5 | 0.01–0.5 |

*available oxygen

PROCESS CONDITIONS

The reaction is conducted at a temperature in the range of about 80° to about 200° C., preferably about 90° to about 120° C. It is conducted at an oxygen pressure or partial oxygen pressure in the range of about 50 to about 600 psig, preferably about 200 to about 450 psig. The reaction time suitably is in the range of about 1 to about 20 hours, preferably about 2 to about 5 hours.

RECOVERY OF PRODUCT

Any person skilled in the art can recover the product from the reaction mixture using known techniques. In order to provide a more complete teaching the following description is being provided as one example of a suitable product isolation procedure when acetic acid is the solvent.

(1) The hot reaction mixture is filtered to remove any precipitated palladium.

(2) The filtered reaction mixture is cooled to 0°–25° C. to allow the product to crystallize.

(3) The cooled reaction mixture is filtered to isolate the crude product.

If desired, the crude product can be recrystallized from a suitable solvent, such as acetone-hexane.

In order to illustrate the nature of the present invention still more clearly the following examples will be given. It is to be understood, however, that the invention is not to be limited to the specific conditions or details set forth in these examples except insofar as such limitations are specified in the appended claims.

EXAMPLE 1

To a 100 ml stainless steel autoclave equipped with a magnetic stirrer was added 5.0 g (36.7 m mole) of 2,3,6-trimethylphenol, 0.25 g (1.11 m mole) of palladium (II) acetate and 60 ml of acetic acid. The autoclave was pressurized to 400 psig with oxygen gas as the mixture was being stirred and then heated over 35 minutes to 100° C. The stirred reaction mixture was maintained at 100° C. and 400 psig for 3 hours. The autoclave was cooled to 60° C. and the pressure was vented. The reaction mixture, containing a grey-black precipitate (Pd), was filtered affording a yellow solution. A white solid precipitated from this solution upon cooling. After further cooling in an ice-water bath, the precipitate was collected by suction filtration to afford 1.55 g of white crystals mp 214°–218° C. Recrystallization from acetic acid and then from acetone-hexane afforded a white solid mp 219°–223° C. The solid was identified as 2,2', 3,3', 5,5'-hexamethyl-[1,1']-biphenyl-1,4-diol on the basis of carbon-hydrogen analysis, spectroscopic data, and comparison (melting point and nmr spectrum) with an authentic sample of 2,2', 3,3', 5,5'-hexamethyl-[1,1']-biphenyl-1,4-diol prepared by oxidation of 2,3,6-trimethylphenol with ferric chloride. Gas chromatographic analysis of the mother liquor (that which remained after the 1.55 g of crystals had been collected) indicated that the trimethylphenol conversion was approximately 40 percent.

EXAMPLE 2

To a 100 ml stainless steel autoclave equipped with a magnetic stirrer was added 5.0 g (36.7 m mole) of 2,3,6-trimethylphenol, 0.25 g (1.11 m mole) of palladium (II) acetate, and 66.4 g of acetic acid. The autoclave was pressurized to 400 psig with oxygen gas as the mixture was being stirred and was then heated to 100° C. over 25 minutes. The stirred reaction mixture was maintained at 100° C. and 400 psig for 3 hours. The autoclave was cooled and then vented. The reaction mixture was warmed to 140° F. for a few minutes to dissolve all of the product which had partially precipitated. The reaction mixture was analyzed by gas chromatography. The analysis indicated that 34 percent of the 2,3,6-trimethylphenol had been converted and that 2,2', 3,3', 5,5'-hexamethyl-[1,1']-biphenyl-1,4-diol was formed in 86 percent selectivity.

Thus, having described the invention in detail, it will be understood by those skilled in the art that certain variations and modifications may be made without departing from the spirit and scope of the invention as defined herein and in the appended claims.

I claim:

1. A method of preparing carbon-carbon coupled condensation products of an alkylphenol, wherein said method comprises contacting said alkylphenol with an effective amount of oxygen or an oxygen-containing gas in the presence of an effective amount of palladium acetate catalyst in a polar solvent which solubilizes palladium acetate under reaction-promoting conditions, said process being characterized further in that:

(A) the alkylphenol is in the group represented by the formula

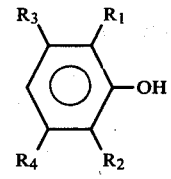

wherein $R_1$, $R_2$, $R_3$ and $R_4$ are hydrogen or $C_1$–$C_4$ alkyl, with at least two alkyls being present one of which is $R_3$ or $R_4$, and (B) the amounts of materials are as follows, on a molar basis: phenol—1.0; oxygen—about 2.5 to about 100; polar solvent—about 2 to about 30, and palladium acetate—about 0.001 to about 0.5.

2. The method of claim 1 wherein the reaction-promoting conditions are:

| | |
|---|---|
| Temperature | about 80 to about 200° C. |
| Pressure (oxygen pressure or partial oxygen pressure) | about 50 to about 600 psig |
| Reaction time | about 1 to about 20 hrs |

3. The method of claim 2 wherein the polar solvent is selected from the group consisting of acetic acid, $C_1$–$C_3$ alkanols, acetonitrile and N,N-dimethylformamide.

4. The method of claim 3 wherein the polar solvent is acetic acid.

5. The method of claim 4 wherein the alkylphenol is represented by the formula

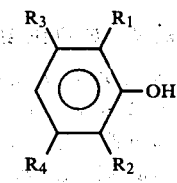

wherein $R_1$, $R_2$, $R_3$ and $R_4$ are hydrogen or $C_1$–$C_4$ alkyl, with at least three alkyl groups being present.

6. The method of claim 1 wherein the amounts of material, on a molar basis, are: phenol—1.0; oxygen—about 10 to about 50; polar solvent—about 4.5 to about 30; palladium acetate—about 0.01 to about 0.5.

7. The method of claim 6 wherein the reaction-promoting conditions are

| | |
|---|---|
| Temperature | about 90 to about 120° C. |
| Pressure (oxygen pressure or partial oxygen pressure) | about 200 to about 450 psig |
| Reaction time | about 2 to about 5 hrs |

8. The method of claim 7 wherein the polar solvent is selected from the group consisting of acetic acid, $C_1$–$C_3$ alkanols, acetonitrile and N,N-dimethylformamide.

9. The method of claim 8 wherein the polar solvent is acetic acid.

10. The method of claim 9 wherein $R_1$, $R_2$, $R_3$ and $R_4$ are hydrogen or methyl, with at least two methyl groups being present one of which is $R_3$ or $R_4$.

11. The method of claim 9 wherein the alkylphenol is represented by the formula

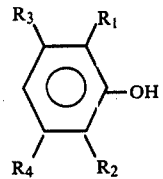

wherein $R_1$, $R_2$, $R_3$ and $R_4$ are hydrogen or $C_1$–$C_4$ alkyl, with at least three alkyl groups being present.

12. The method of claim 11 wherein the alkylphenol is 2,3,6-trimethylphenol.

* * * * *